United States Patent [19]

Silvis et al.

[11] Patent Number: 5,288,113
[45] Date of Patent: Feb. 22, 1994

[54] CONNECTOR FOR CAPILLARY TUBES HAVING A TAPERED INNER BORE

[75] Inventors: Paul H. Silvis, Boalsburg; Bradley R. Rightnour, Mingoville; Richard A. Morehead, Pleasant Gap, all of Pa.

[73] Assignee: Restek Corporation, Bellefonte, Pa.

[21] Appl. No.: 996,697

[22] Filed: Dec. 24, 1992

[51] Int. Cl.[5] .................. F16L 25/00; F16L 35/00
[52] U.S. Cl. ...................... 285/342; 285/334.4; 285/353; 285/911; 285/371; 285/93
[58] Field of Search .......... 285/334.4, 341, 342, 285/343, 353, 354, 371, 911, 93

[56] References Cited

U.S. PATENT DOCUMENTS

| | | | |
|---|---|---|---|
| 823,944 | 6/1906 | Hart | 285/342 |
| 2,669,465 | 2/1954 | Newell | 285/371 |
| 3,866,958 | 2/1975 | Gold | 285/382.2 |
| 4,529,230 | 7/1985 | Fatula, Jr. . | |
| 4,619,473 | 10/1986 | Someya . | |
| 4,690,437 | 9/1987 | Anderson, Jr. . | |
| 4,776,618 | 10/1988 | Barree . | |
| 4,787,656 | 11/1988 | Ryder et al. . | |
| 4,888,990 | 12/1989 | Bryan et al. . | |
| 4,991,883 | 2/1991 | Worden . | |
| 5,163,722 | 11/1992 | Worden | 285/342 |
| 5,234,235 | 8/1993 | Worden | 285/353 |

OTHER PUBLICATIONS

Simple Press-Fit Connectors for Flexible Fused Silica Tubing in Gas-Liquid Chromatography; V. Pretorius and P. J. Apps May 1986 pp. 295-297.
A Simple, Universal Joining System for Glass to Silica Capillary Tubing; A. Spark May 14, 1986; pp. 481-482.
Call for Fused Silica Tubing Furnishing Tight Press-Fit Connections Grob, Bernath, and Neukom; Sep. 1992, pp. 613-614.

*Primary Examiner*—Eric K. Nicholson
*Attorney, Agent, or Firm*—John F. A. Earley; John F. A. Earley, III

[57] ABSTRACT

An easily-assembled, heat-resistant connector for releasably joining end portions of two capillary tubes in end-to-end fashion for use in chromatography without interrupting fluid flow or interfering with chromatographic results, comprises a cylindrical sleeve which has a bore which tapers toward a center point to form press-fit seals with the tips of two capillary tubes. A first ferrule is mounted on the end portion of a first capillary tube, and a second ferrule is mounted on the end portion of a second capillary tube. A jacket surrounds and contains the sleeve, and a first adjustment screw mounted on the jacket pushes against the first ferrule to deform the ferrule into sealing contact with the outside surface of the first capillary tube and with the inside surface of the sleeve. A second adjustment screw mounted on the jacket pushes against the second ferrule to deform the ferrule into sealing contact with the outside surface of the second capillary tube and with the inside surface of the sleeve. The pressure on the first ferrule may be adjusted individually and independently of the pressure on the second ferrule and the pressure on the second ferrule, may be adjusted individually and independently of the pressure on the first ferrule. The pressure from the ferrules also hold the press-fit seals in sealing contact.

11 Claims, 3 Drawing Sheets

CONNECTOR FOR CAPILLARY TUBES HAVING A TAPERED INNER BORE

BACKGROUND OF THE INVENTION

1. Field of the Invention

The present invention is concerned with connectors for joining together the end portions of capillary tubes for use in a gas chromatograph, for example, and is more particularly concerned with providing a connector between capillary tubes which is easily assembled and has a number of leak-proof seals and provides for uninterrupted flow of the fluids such as a carrier gas that flow through the tubes.

2. Description of the Prior Art

Chromatographers and scientists of various disciplines have a need to connect fused silica or stainless steel tubes in end-to-end fashion with a connector that does not detract from chromatographic properties and does not interfere with the flow of fluids such as a carrier gas through the tubes. The connecting together of the end portions of thin wall fused silica or stainless steel tubes with outside diameters ranging from 0.1 to 1.0 mm and inside diameters ranging from 0.01 to 0.8 mm is difficult because the connection may introduce unswept regions or gaps that cause eddies and flow turbulence. Also, the connector may absorb active compounds which decrease the accuracy of the quantitative and qualitative analysis.

U.S Pat. No. 4,529,230 which issued on Jul. 16, 1985 addressed a number of these problems, and disclosed a connector 10 which used a double tapered Vespel ferrule 13 that aligned and sealed the ends of the capillary tubes 11. However, this connector 10 was difficult to use because it was awkward to assemble. Also, it caused adsorption of basic and other compounds with active functional groups. In addition, prolonged use of this connector at temperatures above 325° C. caused the Vespel ferrule to shrink and leak.

Two publications appeared in 1986, *Simple Press-Fit Connectors for Flexible Fused Silica Tubing in Gas-Liquid Chromatography*, Journal of HRC & CC, Volume 9, May 1986, pp. 295–297, and *A Simple, Universal Joining System for Glass to Silica Capillary Tubing*, Journal of HRC & CC, Volume 9, August 1986, pp. 481–482, which appeared to address most of the problems which occur when trying to connect the tips of two fused silica tubes. The press-fit connectors disclosed by these articles formed a good seal and no loss of inertness or adsorption of active analytes occurred. However, this technique was not dependable or reproducible. Sometimes the tubes disconnected unpredictably or leaked. Sometimes the connector did not seal because the glass taper was not made properly. However, a big problem was that these connectors would not function above about 325° C. because the polyimide coating on the flexible fused silica tubing would dry out and loose its sealing ability.

SUMMARY OF THE INVENTION

Accordingly, it is an object of this invention to overcome the problems of prior art connectors which join two capillary tubes together.

It is another object of the present invention to provide a connector with secure seals that incorporate Vespel, a trademark of DuPont, polyimide or graphite ferrules.

It is another object to provide a connector which is free of dead spaces.

It is another object to provide a connector which does not detract from the inertness of the system.

It is another object to provide a connector which overcomes the unpredictability of connectors which utilize compressive forces solely at the tip of the tubes.

It is another object to provide a connector with seals that may be observed visually, and the integrity of the seals determined without requiring chromatographic testing.

It is another object to provide a connector which is reliable and easy to use.

It is another object to provide a connector that may be used at high temperatures, even temperatures exceeding 500° C.

It is another object to provide a connector which has independent adjustment screws for individually controlling the sealing pressure on each capillary tube.

DETAILED DESCRIPTION OF THE DRAWINGS

Figure 1:
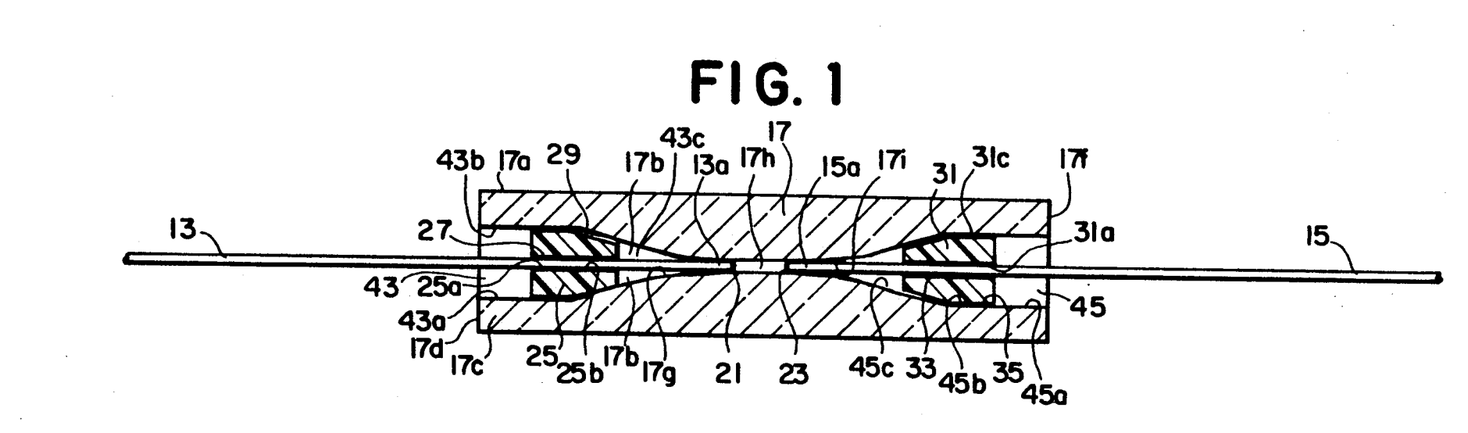
FIG. 1 is a view in longitudinal section of an interior portion of a connector constructed in accordance with this invention.
Figure 2:
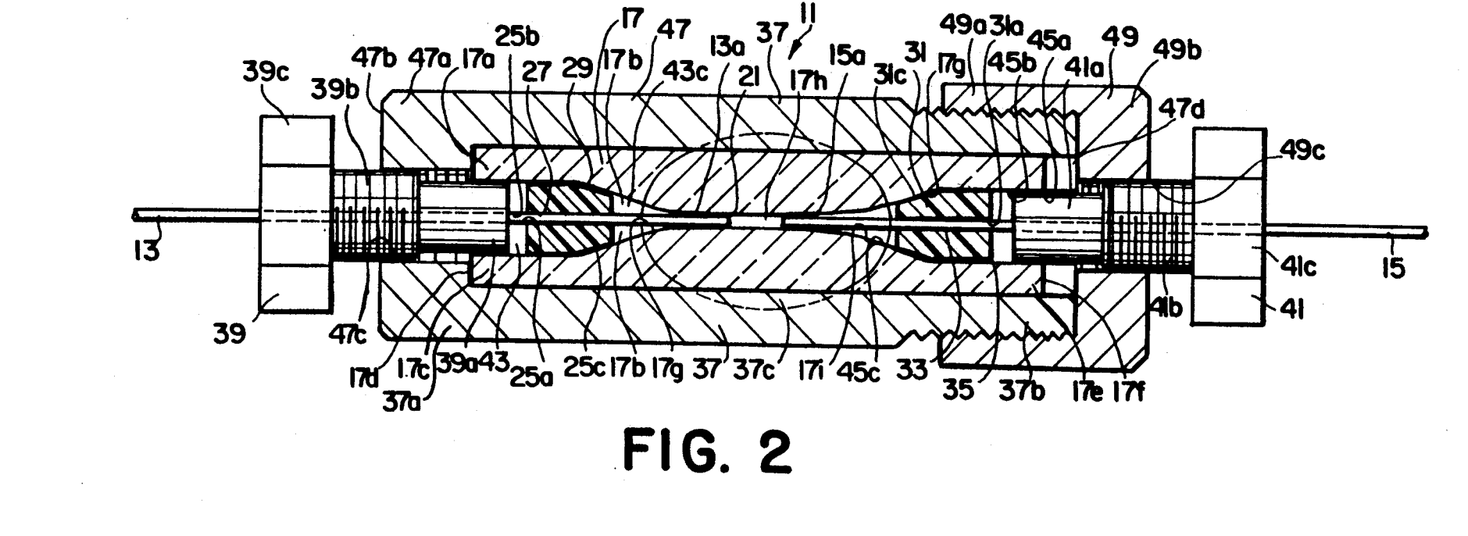
FIG. 2 is a view in elevation and partly in section of the entire connector of FIG. 1.

The Embodiment of FIGS. 1 and 2

Turning now to the drawings, there is shown in FIGS. 1 and 2 an easily-assembled, heat-resistant connector 11 for releasably joining end portion 13a of the tube 13 to end portion 15a of capillary tube 15 in end-to-end fashion for use in chromatography without interrupting fluid flow or interfering with chromatographic results. Both tubes 13 and 15 have a polyimide coating on the outer surface of the tubes.

The connector comprises a cylindrical sleeve 17, which is preferably made of glass although other materials may be used, which has an outside surface 17a and an outside diameter. A bore 17b in sleeve 17 extends between a sleeve first end portion 17c with a first outer end 17d, and a sleeve second end portion 17e which has a second outer end 17f.

The bore 17b also has a first tapered inside surface 17g and a center point 17h.

The first tapered inside surface 17g tapers to a smaller diameter as the bore approaches the center point 17h.

The first tapered inside surface 17g is adapted to be contacted by the tip of end portion 13a of tube 13 to form a press-seal 21 therewith.

The second end portion 17e of the bore 17b has a second tapered inside surface 17i which tapers to a smaller diameter as the bore 17b approaches the center point 17h. The second tapered inside surface 17i is adapted to be contacted by the tip of end portion 15a of the second capillary tube 15 to form a seal 23 therewith.

A first ferrule 25 is mounted on the end portion 13a of the first capillary tube 13, and the first ferrule 25 has a ferrule bore 25a with an inside surface 25b for contacting the outside surface of the first capillary tube 13 to form a seal 27 therewith and first ferrule 25 also has an outside surface 25c for contacting the inside surface of the bore 17b to form a seal 29 therewith.

A second ferrule 31 is mounted on the end portion 15a of second capillary tube 15 and has a ferrule bore 31a with an inside surface for contacting the outside surface of the second capillary tube 15 to form a seal 33 therewith, and has an outside surface 31c contacting the inside surface 17g of bore 17b to form a seal 35 therewith.

A jacket 37 is provided that surrounds and contains the sleeve 17 and has a jacket first end 37a and a jacket second end 37b.

A first adjustment screw 39 is mounted on the jacket first end 37a for pushing against the first ferrule 25 to deform the ferrule 25 into sealing contact with the outside surface of the first capillary tube 13 and with the inside surface of the bore 17b.

A second adjustment screw 41 is mounted on the jacket second end 37b for pushing against the second ferrule 31 to deform the ferrule into sealing contact with the outside surface of the second capillary tube 15 and with the inside surface of the bore 17b.

With this adjustment screw arrangement, the pressure on the first ferrule 25 may be adjusted individually and independently of the pressure on the second ferrule 31. The pressure on first ferrule 25 is adjusted by rotating the first adjustment screw 39 to form seal 27 between the first ferrule 25 and the first tube 13 and to form seal 29 between the first ferrule 25 and the inside surface of sleeve 17. Similarly, the pressure on the second ferrule 31 may be adjusted individually and independently of the pressure on the first ferrule 25 by rotating the second adjustment screw 41 to form seal 33 between the second ferrule 31 and the second tube 15 and a seal 31c between the second ferrule 31 and the inside surface of sleeve 17.

Referring to FIGS. 1 and 2, the connector 11 has a sleeve 17 that includes a first chamber 43 at the outer end 17d of the bore 17b with a larger diameter 43a and an inside surface 43b with a flare to a smaller diameter 43c at an inner end of the first chamber 43. A second chamber 45 is positioned at the other outer end 17f of the bore 17b and has a larger diameter 45a and an inside surface 45b with a flare to a smaller diameter 45c at the inner end of the second chamber 45 near the center point 17h.

The first ferrule 25 is seated in the first chamber 43 and has an outer surface 25c with a flare to a smaller diameter at the inner end of the first chamber 43 to match the flare of the inside surface 43b of the first chamber 43.

The second ferrule 31 is seated in the second chamber 45 and has an outside surface 31c with a flare to a smaller diameter near the inner end of the second chamber 45 to match the flare of the inside surface 45b of the second chamber 45.

Now referring to FIG. 2, jacket 37 includes a cup-shaped housing 47 with a cylindrical sidewall 47a extending from a housing end wall 47b having a threaded hole 47c which is smaller in diameter than the outside diameter of the sleeve 17 in order to hold the sleeve 17 inside the jacket 37.

Housing 47 has an open top 47d which is of larger diameter than the outside diameter of the sleeve 17 so as to receive the sleeve 17 into the housing 47.

A cap 49 is removeably mounted on the open top 47d of the housing and has a sidewall 49a extending from an end wall 49b with a threaded hole 49c which is smaller in diameter than the outside diameter of the sleeve 17 to hold the sleeve 17 inside the jacket 37.

First adjustment screw 39 is hollow to admit the passage of tube 13 and is provided with a stem 39a for exerting pressure on the first ferrule 25, a threaded portion 39b for threading into the threaded hole 47c of housing end wall 47b, and a head 39c for rotating the adjustment screw 39 to adjust the pressure on the first ferrule 25.

Second adjustment screw 41 is hollow to admit the passage of tube 15 and includes a stem 41a for exerting pressure on the second ferrule 31, a threaded portion 41b for threading the second screw 41 into the threaded hole 49c of cap 49, and a head 41c for rotating the second screw 41 to adjust the pressure on the second ferrule 31.

Jacket 37 is provided with visual means for inspecting the seals, and in FIG. 2, those visual means is shown as a window 37c formed in the sidewall 47a of the jacket housing 47.

Alternatively, the housing 47 of the jacket 37 may be made of a heat resistant transparent material such as a clear plastic so as to provide visual means for inspecting the seals.

In operation, the method of connecting and sealing an end portion 13a of a first capillary tube 13 to an end portion 15a of a second capillary tube 15 comprises the steps of providing connector 11, with the parts being unassembled. The end portion 13a of the first capillary tube 13 is inserted through the first adjustment screw 39, through the threaded hole 47c in the housing end wall 47b, through the bore 25a of the first ferrule 25, and into the tapered inside surface of the bore 17b of the sleeve 17 of jacket 37 to form press-seal 21 between the tip of capillary tube 13 and the inner surface of the bore 17b.

Then the end portion 15a of the second capillary tube 15 is inserted through the second adjustment screw 41, through the hole 49c in the cap 49, and through the second ferrule 31, and into the tapered inside surface of the bore 17b to form a press-seal 23 between the tip of the second capillary tube 15 and the sleeve bore 17b.

The cap 49 is then rotated to thread it onto the open top 47d of the jacket housing 47.

Next, the first adjustment screw 39 is independently rotated to adjust the pressure on the first ferrule 25 to form seal 27 between the first ferrule 25 and the first capillary tube 13 and to form seal 29 between the outer surface of first ferrule 25 and the inside surface of sleeve bore 17b.

Then the second adjustment screw 41 is rotated to adjust the pressure on the second ferrule 31 to form seal 33 between the second ferrule 31 and the second capillary tube 15 and to form seal 35 between the second ferrule 31 and the inside surface of sleeve bore 17b.

The integrity of the seals are ascertained by visually inspecting the seals through the window 37c in jacket housing 47.

Figure 3:
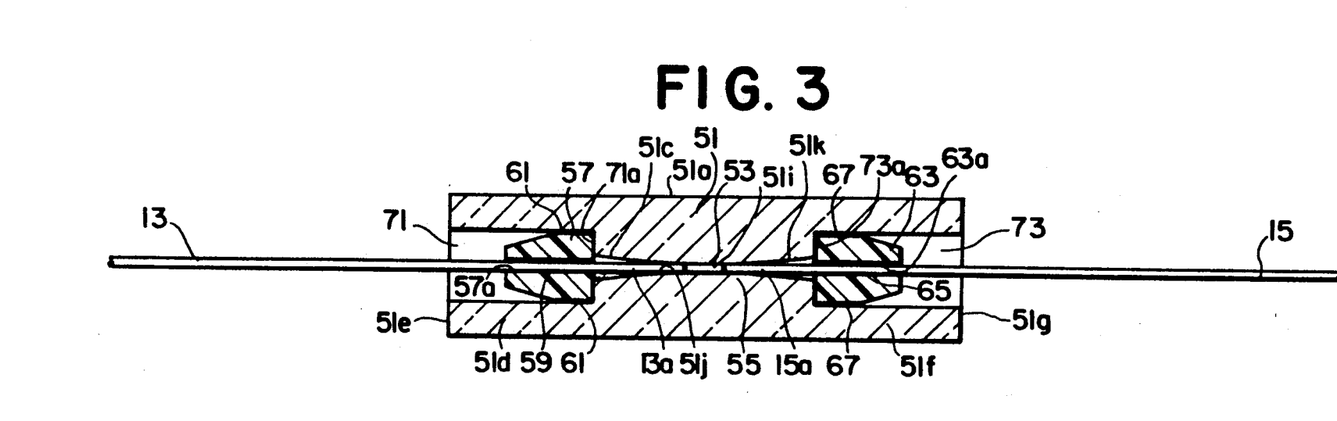
FIG. 3 is a view in longitudinal section of an interior portion of the presently preferred embodiment of the invention.
Figure 4:
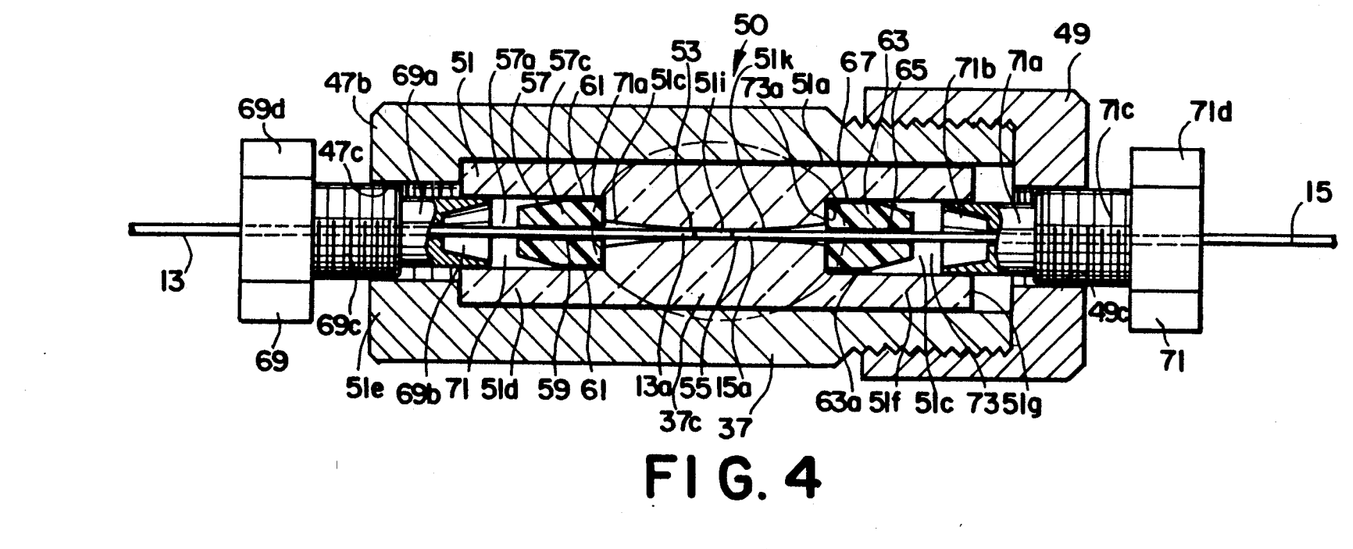
FIG. 4 is a view in elevation and partly in section of the entire presently preferred embodiment of the invention of FIG. 3.

The Embodiment of FIGS. 3 and 4

Turning now to the embodiment of the invention shown in FIGS. 3 and 4, which is the presently preferred embodiment of the invention, there is shown a connector 50 for releasably joining the end portion 13a of capillary tube 13 to the end portion 15a of capillary tube 15 in end-to-end fashion.

Connector 50 includes a cylindrical sleeve 51, preferably made of glass, which has an outside surface 51a and an outside diameter.

Sleeve 51 has a bore 51c with a first end portion 51d and a first outer end 51e, and a second end portion 51f with a second outer end 51g.

Bore 51c has an inside surface and a center point 51i.

The first end portion 51d of the bore 51c has a first tapered inside surface 51j which tapers to a smaller diameter near the center point 51i of the bore 51c.

The first tapered inside surface 51j of bore 51c is adapted for being contacted by the tip of tube 13 to form a press-seal 53.

The second end portion 51f of the bore 51c has a second tapered inside surface 51k which tapers to a smaller diameter near the center point 51i of the bore 51c. The second tapered inside surface 51k of the bore 51c is adapted to be contacted by the tip of the second capillary tube 15 to form a press-seal 55.

A first ferrule 57, which may sometimes be called a reverse ferrule because it faces in the reverse direction from the ferrule 25 in FIGS. 1 and 2, is mounted on the end portion 13a of the first capillary tube 13 and is provided with a ferrule bore 57a with an inside surface for contacting the outside surface of the first capillary tube 13 to form a seal 59 therewith and has an outside surface for contacting the inside surface of the sleeve bore 51c to form a seal 61 therewith.

A second ferrule 63 is mounted on second capillary tube 15 and has a ferrule bore 63a with an inside surface for contacting the outside surface of the second capillary tube end portion 15a to form a seal 65 therewith and has an outside surface for contacting the inside surface of the bore 51c to form a seal 67 therewith.

Jacket 37 surrounds and contains the sleeve 51.

A first adjustment screw 69 is mounted on the jacket housing end wall 47b for pushing against the first ferrule 57 to deform the ferrule 57 into sealing contact with the outside surface of the first capillary tube 13 to form seal 59, and with the inside surface of the bore 51c of the sleeve 51 to form seal 61.

A second adjustment screw 71 is mounted on cap end wall 49b for pushing second ferrule 63 into sealing contact with the outside surface of the second capillary tube 15 to form seal 65 with tube 15, and to form seal 67 with the inside surface of the bore 51c of the sleeve 51.

The sleeve 51 of FIGS. 3 and 4 includes a first chamber 71 which is cylindrical in shape and has an inner stop shoulder 71a which is contacted by the inner end wall of first ferrule 57, and a second chamber 73 which is cylindrical in shape and has an inner stop shoulder 73a. The inner end wall of second ferrule 63 abuts against stop shoulder 73a. The center portion of sleeve bore 51c extends between chamber 71 and chamber 73 and tapers from a larger diameter at shoulders 71a, 73a, to a smaller diameter as the bore 51c approaches the center point 51i of the sleeve bore 51c.

First adjustment screw 69 includes a stem 69a which has a recess 69b shaped like the frustum of a cone which fits over the tapered outer end of the first ferrule 57, a threaded portion 69c for threading into the threaded hole 47c of the housing 47 of the jacket 37, and a head 69d for rotating the screw 69 to adjust the pressure on the first ferrule 57.

Second adjustment screw 71 includes a stem 71a having a recess 71b shaped like the frustum of a cone formed in its end which fits over the tapered outer end of the second ferrule 63, a threaded portion 71c for threading into the threaded hole 49c of the cap 49, and a head 71d for rotating the screw 71 to adjust the pressure on the second ferrule 63.

In operation, the method of assembling connector 50 of FIGS. 3 and 4 is similar to the method of assembling the connector 11 of FIGS. 1 and 2, except in connector 50 the ferrules 57, 63 are inserted with their small diameters facing outwardly to receive recess 69b in first adjustment screw 69 and to receive recess 71b in second adjustment screw 71. The reversed ferrule 57, 63 of connector 50 of FIGS. 3 and 4 tends to prevent the tips of the tubes 13 and 15 from being pushed too far into the tapered inside surface of the bore 51c when the ferrules 57, 63 are beind deformed, and reduces the likelihood of crushing the tip of the tube. Stainless steel capillary tubes may also be connected together by connector 50.

Figure 5:
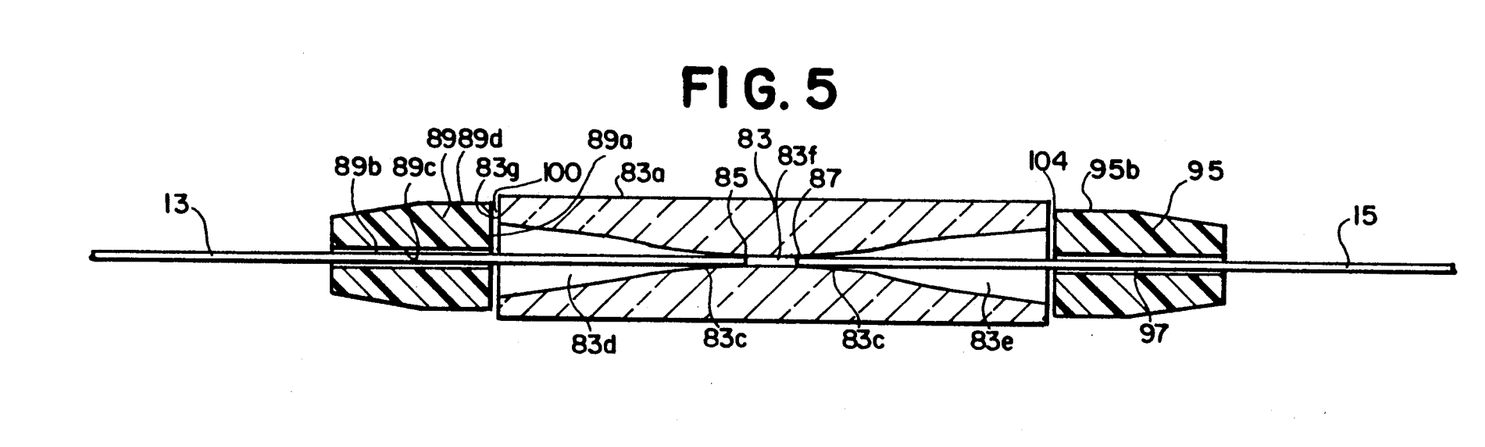
FIG. 5 is a view in longitudinal section of an interior portion of another embodiment of the invention.
Figure 6:
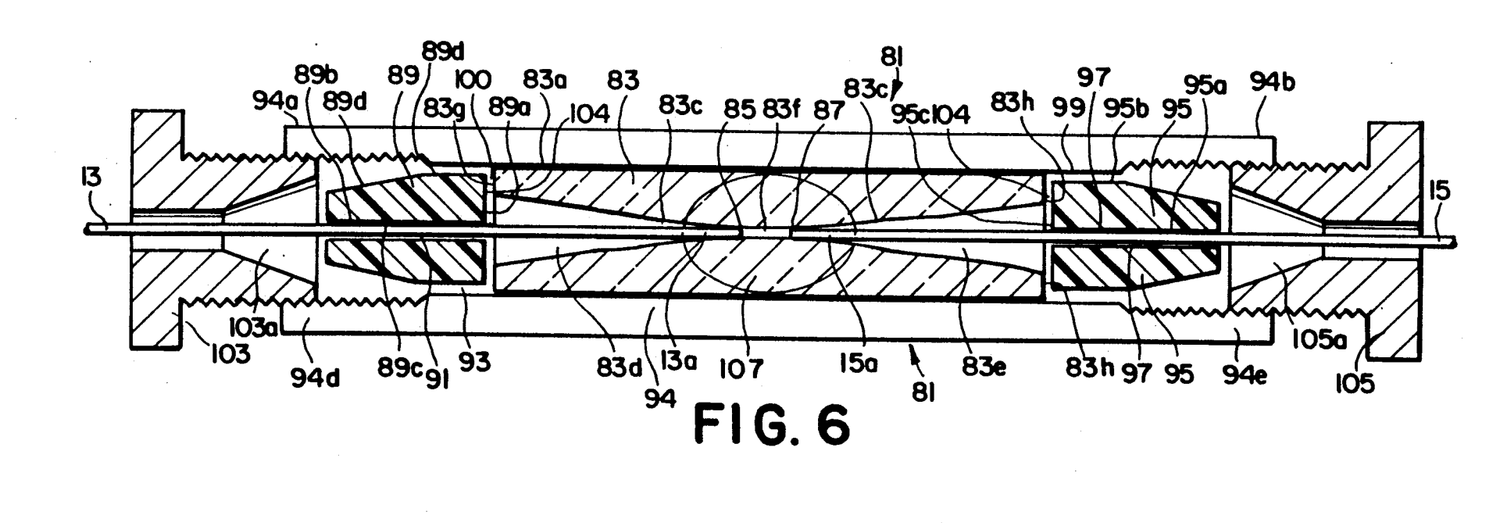
FIG. 6 is a view in elevation and partly in section of the embodiment of FIG. 5.

The Embodiment of FIGS. 5 and 6

The embodiment of the invention disclosed in FIGS. 5 and 6 shows a connector 81 for connecting the end portion 13a of a tube 13 to the end portion 15a of a capillary tube 15.

A cylindrical sleeve 83 is provided having an outside surface 83a and an outside diameter.

A bore 83c in the sleeve 83 extends between a first end chamber 83d and a second end chamber 83e. Bore 83c tapers inwardly toward a smaller diameter at a center point 83f of the bore. The tapered inside surface of the bore 83c is adapted to be contacted by the tip of the end portion 13a of tube 13 to form a press-seal 85 between the bore 83c and the tip of the tube 13.

The taper of bore 83c is also adapted to form a seal 87 with the tip of second capillary tube 15.

A first ferrule 89 is mounted on first tube 13 and has an inner end surface 89a which abuts against the outer end surface 83g of sleeve 83 to form a seal 100.

First ferrule 89 has a bore 89b with an inside surface 89c that forms a seal 91 with the capillary tube 13, and first ferrule 89 has an outside surface 89d that forms a seal 93 with the inside surface of a jacket 94 which fits over the sleeve 83 and the first ferrule 89.

A second ferrule 95 is mounted on the end portion 15a of capillary tube 15 and has a ferrule bore 95a with an inside surface that contacts the outside surface of the second capillary tube 15 to form a seal 97 therewith, and has an outside surface 95b for contacting the inside surface of the jacket 94 sleeve 83 to form a seal 99 therewith.

Second ferrule 95 has an inner end wall 95c that contacts outer end wall 83h of sleeve 83 to form a seal 104 therewith.

A cylindrical jacket 94 surrounds and contains the sleeve 83 and is provided with a threaded first end 94a, and a threaded second end 94b. A threaded first adjustment screw 103 is mounted on the jacket first end 94a and has a frusto-conical recess 103a which receives the tapered end of the ferrule 89. The first adjustment screw 103 pushes against the first ferrule 89 to deform the ferrule into sealing contact with the outside surface of the first capillary tube 13, and with the inside surface of the jacket 94. First screw 103 also pushes ferrule end surface 89a against sleeve end surface 83g to form the seal 100.

A second adjustment screw 105 is threadedly mounted on the jacket second end 94 and has a recess 105a in the shape of a frustum of a cone which receives the tapered end of ferrule 95. The second adjustment screw 105 pushes against the second ferrule 95 to deform the ferrule 95 into sealing contact with the outside surface of the second capillary tube 15 to form seal 97, and into sealing contact with the inside surface of the jacket 94 to form seal 99. Second screw 105 also pushes ferrule end surface 95c against sleeve end surface 83h to form seal 104.

Jacket 94 includes a cylindrical sidewall 94c with a first end portion 94d that overhangs the first ferrule 89, and a cylindrical side wall 94e that overhangs the second ferrule 95.

In operation, the method of assembling the connector 81 of FIGS. 5 and 6 and of sealingly connecting an end portion 13a of a first capillary tube 13 to an end portion 15a of a second capillary tube 15 comprises the steps of providing the unassembled parts of connector 81, and inserting the end portion 13a of first capillary tube 13 through first adjustment screw 103, through first ferrule 89 and into the tapered inside surface of the bore 83c to form a press-seal 85 between the bore 83c and the tip of the tube 13.

Jacket 94 is slipped over sleeve 83 so that jacket end portion 94d overhangs first ferrule 89, and the first adjustment screw 103 is screwed into the overhanging portion 94d of the jacket 94 just enough to hold screw 103 in the jacket.

The end of tube 15 is inserted through the second adjustment screw 105, the second ferrule 95, and the tapered bore 83c of sleeve 83 so that its tip forms a press-seal 87 with the tapered bore 83c.

Second ferrule 95 is positioned in the overhanging portion 94e of jacket 94, and second adjustment screw 105 is rotated and threaded into the overhanging portion 94e of the jacket 94.

The first adjustment screw 103 and second adjustment screw 105 are tightened at the same time so as to not move the glass sleeve 83 or cause the ferrules to pop out of glass sleeve 83.

First adjustment screw 103 is rotated so that its recess 103a in the shape of a frustum of a core receives the tapered outside surface 89d of first ferrule 89 and pushes against first ferrule 89 to deform it to form a seal 91 with the outer surface of tube 13, to form a seal 93 with the inner surface of jacket 94, and to form a seal 104 between the outer surface 83g of sleeve 83 and the inner surface 89a of the first ferrule 89.

The second adjustment screw 105 is rotated to press against the second ferrule 95 and deform it so that its inner surface forms a seal 95a with the tube 15, and so that its outside surface forms a seal 99 with the inner surface of jacket 95. Also, the inner end 95c of ferrule 95 is pushed by the rotation of screw 105 toward the center point 83c so that the inner end 95c of the second ferrule 95 contacts and pushes against the outer end 83h of sleeve 83 to form a seal 104.

The first adjustment screw 103 may be independently rotated a desired to adjust the pressure on first ferrule 89 and thereby adjust the pressure on the seals 85, 100, 91 and 89d, and the second adjustment screw 105 may be independently rotated to adjust the pressure on second ferrule 95 to adjust the pressure on the seals 87, 104, 99 and 97. The adjustment of first adjustment screw 103 is entirely independent of the adjustment of second adjustment screw 105, and the adjustment of second adjustment screw 105 is entirely independent of the adjustment of first adjustment screw 103. The integrity of the seals is ascertained by visually inspecting the seals through the window 107 in jacket 94. Window 87 may be a small oval as shown, or it may be a large rectangular window which allows inspection, not only of the press-fit seals 85 and 87, but also of the seals created by the ferrules 89 and 95. Similarly, window 37c in FIG. 2, and window 37c in FIG. 4, may be larger rectangular windows that allow inspection of all the seals in the jacket.

The integrity of the press-fit seals of the tips of tubes 13 and 15 is ascertainable visually because the operator can see that the tip of the tube is seated in the tapered bore of the sleeve, and because a brown ring forms at the tip of the tubes that tells the operator he has a good seal. The polyimide coating on the outside of the tube makes the brown ring form at its point of contact with the tapered inside surface of the bore of the sleeve.

The ferrules used in this invention are preferably made of VESPEL polyimide available from DuPont under the resin designation SP-21 which is described as 15% by weight graphite encapsulated filler.

The adjustment screws and ferrules hold tight the press-fit seals of the tips of the tubes even if the coating on the tubes deteriorates.

We claim:

1. An easily-assembled, heat-resistant connector for releasably joining end portions of two capillary tubes in end-to-end fashion for use in chromatography without interrupting fluid flow or interfering with chromatographic results, comprising a cylindrical sleeve having an outside surface and an outside diameter, a bore in the sleeve extending between a sleeve first end portion with a first outer end and a sleeve second end portion with a second Outer end, the bore having an inside surface and a center point, the first end portion of the bore having a first tapered inside surface which tapers to a smaller diameter near the center point of the bore, the first tapered inside surface being adapted for being contacted by a tip of an end portion of a first capillary tube to form a press-seal therewith, the second end portion of the bore having a second tapered inside surface which tapers to a smaller diameter near the center point of the bore, the second tapered inside surface of the sleeve being adapted for being contacted by a tip of an end portion of a second capillary tube to form a press-seal therewith, a first ferrule adapted to be mounted on the end portion of the first capillary tube and having a ferrule bore with an inside surface for contacting the outside surface of the first capillary tube to form a seal therewith, and having an outside surface for contacting the inside surface of the sleeve bore to form a seal with the inside surface of the sleeve bore, a second ferrule adapted to be mounted on the end portion of the second capillary tube and having a ferrule bore with an inside surface for contacting the outside surface of the second capillary tube to form a seal therewith, and having an outside surface for contacting the inside surface of the sleeve bore to form a seal therewith, a jacket surrounding and containing the sleeve and having a jacket first end and a jacket second end, a first adjustment screw means mounted on the jacket first end for pushing against the first ferrule to deform the ferrule into sealing contact with the outside surface of the first capillary tube and with the inside surface of the sleeve bore, a second adjustment screw means mounted on the jacket second end for pushing against the second ferrule to deform the ferrule into sealing contact with the outside surface of the second capillary tube and with the inside surface of the sleeve bore, whereby the pressure on the first ferrule may be adjusted individually and independently of the pressure on the second ferrule by rotating the first adjustment screw to form seals between the first ferrule and the first tube and between the first ferrule and the sleeve, and the pressure on the second ferrule may be adjusted individually and independently of the pressure on the first ferrule by rotating the second adjustment screw to form seals between the second ferrule and the second tube and between the second ferrule and the sleeve.

2. The connector of claim 1, said sleeve including a first chamber at an outer end of the sleeve bore with a larger diameter and an inside surface with a taper to a smaller diameter at an inner end of the first chamber, a second chamber at an outer end of the sleeve bore with a larger diameter and an inside surface with a taper to a smaller diameter at an inner end of the second chamber, the first ferrule being seated in the first chamber and having an outside surface with a taper to a smaller diameter at the inner end to match the flare of the first chamber, and the second ferrule being seated in the second chamber and having an outside surface with a taper to a smaller diameter at the inner end to match the flare of the inside surface of the second chamber.

3. The connector of claim 1, said jacket comprising a cup-shaped housing with a cylindrical sidewall extending from a housing end wall having a threaded hole which is smaller in diameter than the outside diameter of the sleeve to hold the sleeve in the housing, the housing having an open top of larger diameter than the outside diameter of the sleeve so as to receive the sleeve into the housing, a cap removably mounted on the open top of the housing and having a sidewall extending from an end wall with a threaded hole which is smaller in diameter than the outside diameter of the sleeve to hold the sleeve in the jacket.

4. The connector of claim 3, said first adjustment screw means comprising a first adjustment screw with a stem for exerting pressure on the first ferrule, a threaded portion for threading into the threaded hole of the housing end wall, and a head for rotating the adjustment screw to adjust the pressure on the first ferrule, said second adjustment screw means comprising a second adjustment screw with a stem for exerting pressure on the second ferrule, a threaded portion for threading the second screw into the threaded hole of the cap, and a head for rotating the second screw to adjust the pressure on the second ferrule.

5. The connector of claim 1, said jacket having visual means for inspecting the seals of the connector.

6. The connector of claim 5, said visual means being a window formed in the sidewall of the jacket.

7. The connector of claim 5, said visual means being a jacket made of transparent material.

8. An easily-assembled, heat-resistant capillary tube connector for releasably joining end portions of two capillary tubes in end-to-end fashion for use in chromatography without interrupting fluid flow or interfering with chromatographic results, comprising a cylindrical sleeve having an outside surface and an outside diameter, a bore in the sleeve extending between a sleeve first end portion with a first outer end and a sleeve second end portion with a second outer end, the bore having an inside surface and a center point, the first end portion of the sleeve having a first tapered inside surface which tapers to a smaller diameter near the center point of the sleeve, the first tapered inside surface of the sleeve being adapted for being contacted by a tip of an end portion of a first capillary tube to form a press-seal therewith, the second end portion of the sleeve having a second tapered inside surface which tapers to a smaller diameter near the center point of the bore, the second tapered inside surface of the sleeve being adapted for being contacted by a tip of an end portion of a second capillary tube to from a press-seal therewith, a first ferrule adapted to be mounted on the end portion of the first capillary tube and having a ferrule bore with an inside surface for contacting the outside surface of the first capillary tube to form a seal therewith, and having an outside surface for contacting the inside surface of the sleeve bore to form a seal with the inside surface of the sleeve, a second ferrule adapted to be mounted on the end portion of the second capillary tube and having a ferrule bore with an inside surface for contacting the outside surface of the second capillary tube to form a seal therewith, and having an outside surface for contacting the inside surface of the sleeve bore to form a seal therewith, a jacket surrounding and containing the sleeve and having a jacket first end and a jacket second end, a first adjustment screw means mounted on the jacket first end for pushing against the first ferrule to deform the ferrule into sealing contact with the outside surface of the first capillary tube and with the inside surface of the sleeve bore, a second adjustment screw means mounted on the jacket second end for pushing against the second ferrule to deform the ferrule into sealing contact with the outside surface of the second capillary tube and with the inside surface of the sleeve bore, whereby the pressure on the first ferrule may be adjusted individually and independently of the pressure on the second ferrule by rotating the first adjustment screw to form seals between the first ferrule and the first tube and between the first ferrule and the sleeve, and the pressure on the second ferrule may be adjusted individually and independently of the pressure on the first ferrule by rotating the second adjustment to form seals between the second ferrule and the second tube and between the second ferrule and the sleeve, said sleeve including a first chamber at an outer end of the sleeve bore with a larger diameter and an inside surface with a taper to a smaller diameter at an inner end of the first chamber, a second chamber at an outer end of the sleeve bore with a larger diameter and an inside surface with a taper to a smaller diameter at an inner end of the second chamber, the first ferrule being seated in the first chamber and having an outside surface with a taper to a smaller diameter at the inner end to match the flare of the first chamber, and the second ferrule being seated in the second chamber and having an outside surface with a taper to a smaller diameter at the inner end to match the flare of the second chamber, said jacket comprising a cup-shaped housing with a cylindrical sidewall extending from a housing end wall having a threaded hole which is smaller in diameter than the outer diameter of the sleeve to hold the sleeve in the jacket housing, the housing having an open top of larger diameter than the outside diameter of the sleeve so as to receive the sleeve into the housing, a cap removably mounted on the open top of the housing and having a sidewall extending from an end wall with a threaded hole which is smaller in diameter than the outer diameter of the sleeve to hold the sleeve in the jacket, said first adjustment screw means comprising a first adjustment screw with a stem for exerting pressure on the first ferrule, a threaded portion for threading into the threaded hole of the housing end wall, and a head for rotating the adjustment screw to adjust the pressure on the first ferrule, said second adjustment screw means comprising a second adjustment screw with a stem for exerting pressure on the second ferrule, a threaded portion for threading the second screw into the threaded hole of the cap, and a head for rotating the second screw to adjust the pressure on the second ferrule, and said jacket having visual means for inspecting the seals of the connector.

9. A method of sealingly connecting an end portion of a first capillary tube to an end portion of a second capillary tube, comprising the steps of providing an easily-assembled, heat-resistant capillary tube connector for releasably joining end portions of two capillary tubes in end-to-end fashion for use in chromatography without interrupting fluid flow or interfering with chromatographic results, comprising a cylindrical sleeve having an outside surface and an outside diameter, a bore in the sleeve extending between a sleeve first end portion with a first outer end and a sleeve second end portion with a second outer end, the bore having an inside surface and a center point, the first end portion of the sleeve having a first tapered inside surface which tapers to a smaller diameter near the center point of the sleeve, the first tapered inside surface of the sleeve being adapted for being contacted by a tip of an end portion of a first capillary tube to form a press-seal therewith, the second end portion of the sleeve having a second tapered inside surface which tapers to a smaller diameter near the center point of the sleeve, the second tapered inside surface of the sleeve being adapted for being contacted by a tip of an end portion of a second capillary tube to form a press-seal therewith, a first ferrule adapted to be mounted on the end portion of the first capillary tube and having a ferrule bore with an inside surface for contacting the outside surface of the first capillary tube to form a seal therewith, and having an outside surface for contacting the inside surface of the sleeve bore to form a seal with the inside surface of the sleeve, a second ferrule adapted to be mounted on the end portion of the second capillary tube and having a ferrule bore with an inside surface for contacting the outside surface of the second capillary tube to form a seal therewith, and having an outside surface for contacting the inside surface of the sleeve bore to form a seal therewith, a jacket surrounding and containing the sleeve and having a jacket first end and a jacket second end, a first adjustment screw means mounted on the jacket first end for pushing against the first ferrule to deform the ferrule into sealing contact with the outside surface of the first capillary tube and with the inside surface of the sleeve bore, a second adjustment screw means mounted on the jacket second end for pushing against the second ferrule to deform the ferrule into sealing contact with the outside surface of the second capillary tube and with the inside surface of the sleeve bore, whereby the pressure on the first ferrule may be adjusted individually and independently of the pressure on the second ferrule by rotating the first adjustment screw to form seals between the first ferrule and the first tube and between the first ferrule and the sleeve, and the pressure on the second ferrule may be adjusted individually and independently of the pressure on the first ferrule by rotating the second adjustment to form seals between the second ferrule and the second tube and between the second ferrule and the sleeve, said sleeve including a first chamber at an outer end of the sleeve bore with a larger diameter and an inside surface with a taper to a smaller diameter at an inner end of the first chamber, a second chamber at an outer end of the sleeve bore with a larger diameter and an inside surface with a taper to a smaller diameter at an inner end of the second chamber, the first ferrule being seated in the first chamber and having an outside surface with a taper to a smaller diameter at the inner end to match the flare of the first chamber, and the second ferrule being seated in the second chamber and having an outside surface with tpaer to a smaller diameter at the inner end to match the flare of the second chamber, said jacket comprising a cup-shaped housing with a cylindrical sidewall extending from a housing end wall having a threaded hole which is smaller in diameter than the outer diameter of the sleeve to hold the sleeve in the jacket housing, the housing having an open top of larger diameter than the outside diameter of the sleeve so as to receive the sleeve into the housing, a cap removably mounted on the open top of the housing and having a sidewall extending from an end wall with a threaded hole which is smaller in diameter than the outer diameter of the sleeve to hold the sleeve in the jacket, said first adjustment screw means comprising a first adjustment screw with a stem for exerting pressure on the first ferrule, a threaded portion for threading into the threaded hole of the housing end wall, and a head for rotating the adjustment screw to adjust the pressure on the first ferrule, said second adjustment screw means comprising a second adjustment screw with a stem for exerting pressure on the second ferrule, a threaded portion for threading the second screw into the threaded hole of the cap, and a head for rotating the second screw to adjust the pressure on the second ferrule, and said jacket having visual means for inspecting the seals, inserting the end portion of the first capillary tube through the first adjustment screw, through the threaded hole of the jacket housing end wall, through the first ferrule, and into the tapered inside surface of the sleeve in the housing to form a press-seal between the tip of the capillary tube and the inner surface of the sleeve bore, inserting the end portion of the second capillary tube through the second adjustment screw, through the hole in the cap, and through the second ferrule and into the tapered inside surface of the sleeve to form a press-seal between the tip of the capillary tube and the inner surface of the sleeve bore, rotating the cap to mount it onto the open top of the jacket housing, independently rotating the first adjustment screw to adjust the pressure on the first ferrule to form a seal between the first ferrule and the first capillary tube and to form a seal between the first ferrule and the sleeve bore, independently rotating the second adjustment screw to adjust the pressure on the second ferrule to form a seal between the second ferrule and the second capillary tube and to form a seal between the second ferrule and the sleeve, and visually inspecting the seals.

10. The connector of claim 1, said sleeve including a first chamber having an inner stop shoulder for contacting the first ferrule, a second chamber having an inner stop shoulder for contacting the second ferrule, a bore extending between the first and second chamber and tapering to a smaller diameter near the center point of the bore, the first ferrule being seated in the first chamber with a tapered surface which tapers to a smaller diameter at its outer end, a second ferrule being seated in the second chamber with a tapered surface which tapers to a smaller diameter at its outer end, said first adjustment means including a first adjustment screw with a stem having a frusto-conical shaped recess adapted to fit over the tapered outer end of the first ferrule, a threaded portion for threading into the threaded hole of the housing end wall, and a head for rotating the screw to adjust the pressure on the first ferrule, said second adjustment screw means including a second adjustment screw with a stem having a frusto-conical shaped recess adapted to fit over the tapered outer end of the second ferrule, a threaded portion for threading into the threaded hole of the cap, and a head for rotating the screw to adjust the pressure on the second ferrule.

11. The connector of claim 1, said jacket comprising said housing having a cylindrical sidewall with a first end portion that overhangs a first ferrule with an inner end in abutment with the first end portion of the sleeve, said first ferrule having an outer end portion which tapers to a smaller diameter at its outer end, said first adjustment screw means including a first adjustment screw with a stem having a frusto-conical shaped recess adapted to fit over the tapered outer end of the first ferrule, a threaded portion for threading into the first end portion of the jacket, and a head for rotating the screw to adjust the pressure on the first ferrule, said second ferrule having an outer end portion which tapers to a smaller diameter at its outer end, said housing having a cylindrical sidewall with a second end portion that overhangs a second ferrule with an inner end in abutment with the second end portion of the sleeve, said second adjustment screw means including a second adjustment screw with a stem having a frusto-conical shaped recess adapted to fit over the tapered outer end of the second ferrule, a threaded portion for threading into the second end portion of the jacket, and a head for rotating the screw to adjust the pressure on the second ferrule, whereby the adjustment screws are individually adapted to exert pressure on the ferrules to squeeze them against the outer surface of the capillary tubes and against the inner surface of the end portions of the jackets, and push the ferrules against the outer end surfaces of the sleeves to seal the connector.

* * * * *